United States Patent
Bannister

(10) Patent No.: US 7,910,118 B2
(45) Date of Patent: Mar. 22, 2011

(54) SKIN TREATMENT

(76) Inventor: Dennis R. Bannister, Columbia, SC (US)

( * ) Notice: Subject to any disclaimer, the term of this patent is extended or adjusted under 35 U.S.C. 154(b) by 1654 days.

(21) Appl. No.: 10/892,586

(22) Filed: Jul. 16, 2004

(65) Prior Publication Data

US 2006/0013841 A1     Jan. 19, 2006

(51) Int. Cl.
*A61K 8/00* (2006.01)
(52) U.S. Cl. ........................................ 424/401
(58) Field of Classification Search .................. None
See application file for complete search history.

(56) References Cited

U.S. PATENT DOCUMENTS

| 4,082,850 | A |   | 4/1978 | Lassman et al. |
| 4,342,743 | A | * | 8/1982 | Panton-Moore ............... 424/61 |
| 4,654,213 | A |   | 3/1987 | Ramirez et al. |
| 4,732,759 | A |   | 3/1988 | Shibanai et al. |
| 5,774,909 | A |   | 7/1998 | Stable |
| 5,783,601 | A |   | 7/1998 | Tanahashi et al. |
| 5,958,462 | A |   | 9/1999 | McLean |
| 5,968,539 | A | * | 10/1999 | Beerse et al. ............... 424/405 |
| 6,066,607 | A |   | 5/2000 | Gordon et al. |
| 6,142,156 | A |   | 11/2000 | Brunderman |
| 6,168,852 | B1 |   | 1/2001 | Smith, III et al. |
| 6,511,955 | B1 |   | 1/2003 | Drapier et al. |
| 6,544,534 | B2 |   | 4/2003 | Malmgren et al. |
| 7,264,795 | B2 | * | 9/2007 | Pflucker et al. ............... 424/59 |
| 2003/0190371 | A1 | * | 10/2003 | Graaf et al. ............... 424/642 |
| 2004/0076694 | A1 | * | 4/2004 | Lia ............................... 424/747 |

* cited by examiner

*Primary Examiner* — Robert A Wax
*Assistant Examiner* — Melissa S Mercier
(74) *Attorney, Agent, or Firm* — Nexsen Pruet, LLC; Sara Centioni Kanos

(57) ABSTRACT

A solution for the treatment of human feet. The solution includes an amount of each of the following components: 1) magnesium sulfate, 2) water, 3) methylparaben, 4) isopropyl alcohol, 5) methyl salicylate, and 6) malic acid. In combination, these components form an aqueous solution, which can be used as part of a footbath for soaking, or which can be applied directly to the foot using an applicator, such as a wipe.

9 Claims, 2 Drawing Sheets

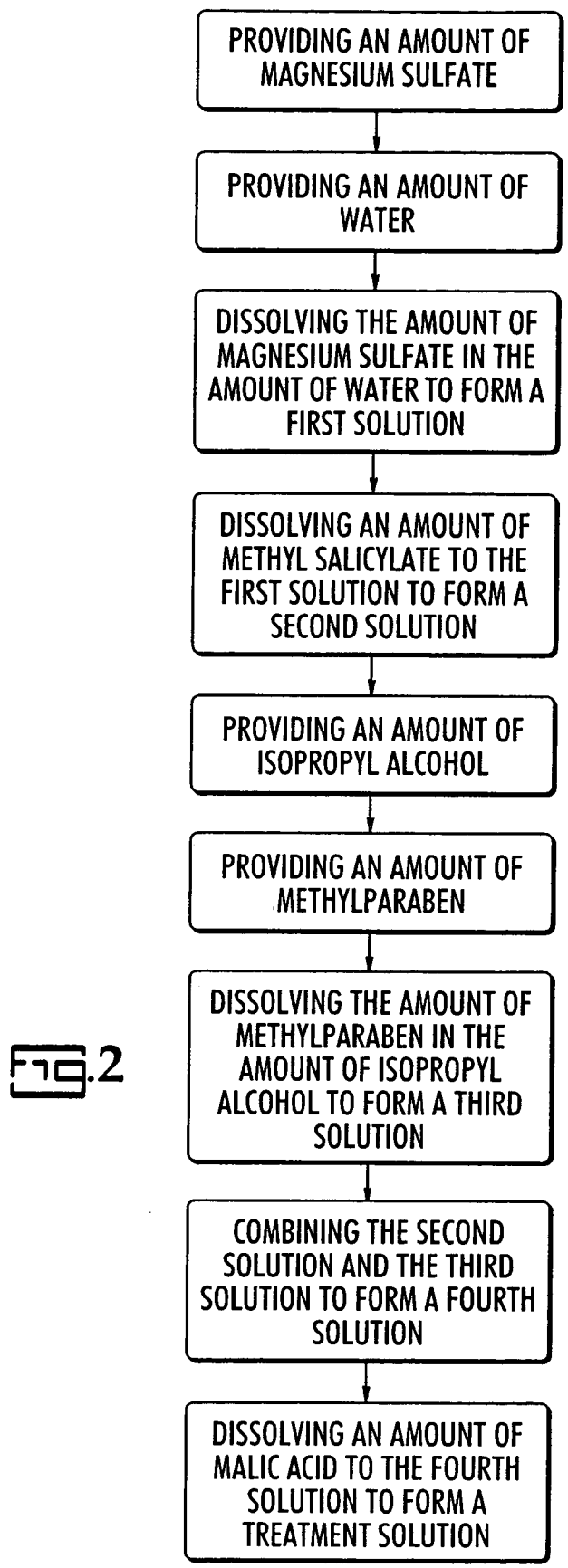

SKIN TREATMENT

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A SEQUENCE LISTING, A TABLE, OR A COMPUTER PROGRAM LISTING COMPACT DISK APPENDIX

Not Applicable.

BACKGROUND OF THE INVENTION

Generally, the present invention relates to skin treatment products, and, more particularly, to a solution used in the treatment of human feet.

Many products and methods for treatment have been developed for use on the treatment of problems associated with human feet. It is known that when feet are subjected to prolonged friction and pressure, excess skin can build upon the foot so as to create calluses and corns. Furthermore, feet can become irritated and swollen through over exertion. Finally, the region of skin associated with feet is the most likely to retain dirt considering it is most often placed in contact with soiled surfaces such as the ground.

Whereas some products and devices are effective at relieving certain problems associated with human feet, these products are typically inadequate at relieving all of the problems. Further, the products tend to be expensive and inconvenient for everyday use. For example, medicated pads may prevent further irritation and callous growth, but they typically do not alleviate existing foot problems. Additionally, the use of pumice stones to remove dead skin, which must usually be done during showering, can be awkward and create safety hazards. Finally, moisturizing feet with the use of lotions typically can only soften feet for a very limited amount of time and cannot remove already existing dead skin from the feet.

Accordingly, there exists a need for an all-inclusive, convenient solution that aids in relieving most, if not all, problems associated with the skin of human feet, including skin hardening, dryness, irritation, and dirt.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

According to its major aspects, and briefly stated, the present invention includes a solution for the treatment of human feet. The solution includes an amount of each of the following components: 1) magnesium sulfate, 2) water, 3) methylparaben, 4) isopropyl alcohol, 5) methyl salicylate, and 6) malic acid. In combination, these components form an aqueous solution that can be used as part of a footbath for soaking, or which can be applied directly to the foot using an applicator, such as a wipe.

A feature of the present invention is the use of magnesium sulfate in the solution. The use of magnesium sulfate is effective in the removal of dirt from feet, as well as in the soothing of any existing swelling and irritation.

Another feature of the present invention is the use of isopropyl alcohol in the solution. Isopropyl alcohol is influential in eliminating bacteria growth in the composition, so that the solution remains hygienic and can enjoy a longer shelf life. Further, isopropyl alcohol helps keep the other components of the solution dissolved in water.

Yet another feature of the present invention is the use of methylparaben in the solution. This component also contributes to the elimination of bacterial growth in the solution.

Still another feature of the present invention is the use of methyl salicylate in the solution. Methyl salicylate adds fragrance to the solution, which provides a soothing and relaxing feeling to the user of the solution. Further, this component also reduces bacterial growth in the solution.

Yet another feature of the present invention is the use of malic acid in the solution. The use of malic acid adds a softener to the solution so as to enable the moisturizing of human feet by the solution.

Other features and advantages of the present invention will be apparent to those skilled in the art from a careful reading of the Detailed Description of the Invention presented below and accompanied by the drawing.

BRIEF DESCRIPTION OF THE DRAWINGS

In the drawings,

FIG. 2 illustrates a flowchart of a method for making a solution for use in the treatment of human feet according to a preferred embodiment of the present invention.

DETAILED DESCRIPTION OF THE PREFERRED EMBODIMENTS

Figure 1:
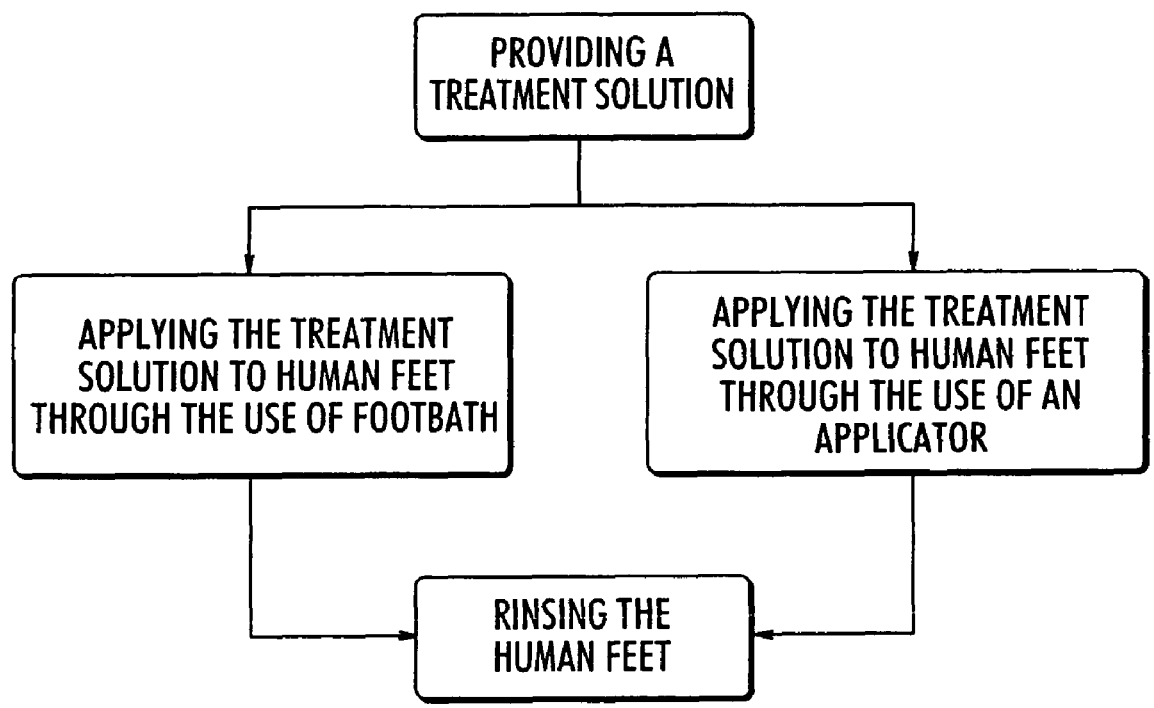
FIG. 1 illustrates a flowchart of a method of treating human feet employing a solution according to a preferred embodiment of the present invention.

The present invention includes a solution for the treatment of problems typically associated with human feet. The solution includes a combination of magnesium sulfate, methylparaben, isopropyl alcohol, methyl salicylate, and malic acid. These components are dissolved in water to form an aqueous solution that can be applied to the human feet to remove dirt, irritation, swelling, and dry skin.

Per one gallon of water, each of the components of the foot treatment solution are dissolved in water in the following amounts: 1) between approximately 40 oz (ounces) and approximately 45 oz of magnesium sulfate; 2) between approximately 0.01 oz and approximately 1.0 oz of methylparaben; 3) between approximately 10 oz and approximately 15 oz of isopropyl alcohol; 4) between approximately 0.05 oz and approximately 1.5 oz of methyl salicylate; and 5) between approximately 0.05 oz and approximately 1.5 oz of malic acid. Preferably, these components are combined in the following amounts per one gallon of water: 1) approximately 43 oz of magnesium sulfate; 2) approximately 0.05 oz of methylparaben; 3) approximately 13 oz of isopropyl alcohol; 4) approximately 0.9 oz of methyl salicylate; and 5) approximately 0.9 oz of malic acid.

The combination of these components into one solution is a particular feature of the present invention. The use of magnesium sulfate, and, particularly, magnesium sulfate hepta-hydrate, $MgSO4.7H2O$, is effective in the removal of dirt from feet, as well as in the soothing of any existing swelling and irritation. Isopropyl alcohol is influential in eliminating bacterial growth in the composition, so that the solution remains hygienic and can enjoy a longer shelf life. Further, isopropyl alcohol helps keep the other components of the solution dissolved in water. Methylparaben also contributes to the elimination of bacterial growth in the solution. Methyl salicylate adds fragrance to the solution, which provides a soothing and relaxing feeling to the user of the solution. Further this component also reduces bacterial growth in the solution. Finally, the use of malic acid adds a softener to the solution so as to enable the moisturizing of human feet by the solution.

In use, the foot treatment solution can be applied directly to the human feet by rinsing the feet with the solution, or by applying the solution using any common applicator, such as a wipe. Additionally, the solution can be added to a footbath so that the feet can be soaked in the solution. In the case that the solution is used as part of a footbath, preferably, the solution can be further diluted with water to create a ratio of solution to water of between approximately 1:10 and approximately 1:20. However, a particular concentration of solution to water is unnecessary to provide an effective treatment of the feet. FIG. 1 illustrates these alternative methods of treatment using the described solution.

Although the various components of the foot care treatment solution can be combined randomly to form the described solution, a preferred method of making the solution includes the following steps (shown in FIG. 2): 1) providing an amount of magnesium sulfate; 2) providing an amount of water; 3) dissolving the amount of magnesium sulfate in the amount of water to form a first solution, wherein the ratio of magnesium sulfate to water is approximately 1:3 by weight; 4) dissolving an amount of methyl salicylate to the first solution to form a second solution; 3) providing an amount of isopropyl alcohol; 4) providing an amount of methylparaben; 5) dissolving the amount of methylparaben in the amount of isopropyl alcohol to form a third solution; 6) combining the second solution and the third solution to form a fourth solution; 7) dissolving an amount of malic acid to the fourth solution to form the treatment solution.

Once the treatment solution has been made, it can be stored at room temperature. Through the use of isopropyl alcohol, methylparaben, and methyl salicylate, the shelf life of the treatment solution can be extended, as these components control bacteria growth in the solution.

It will be apparent to those skilled in the art that many changes and substitutions can be made to the preferred embodiment herein described with departing from the spirit and scope of the present invention as defined by the appended claims.

What is claimed is:

1. A solution for the treatment of human feet, consisting of:
    an amount of water;
    between approximately 40 oz and approximately 45 oz of magnesium sulfate per gallon of said water;
    between approximately 0.01 oz and approximately 1.0 oz of methylparaben per gallon of said water;
    between approximately 10 oz and approximately 15 oz of isopropyl alcohol per gallon of said water;
    between approximately 0.05 oz and approximately 1.5 oz of methyl salicylate per gallon of said water; and
    between approximately 0.05 oz and approximately 1.5 oz of malic acid per gallon of said water.

2. The solution as recited in claim 1, wherein said solution includes approximately 43 oz of said magnesium sulfate.

3. The solution as recited in claim 1, wherein said solution includes approximately 0.05 oz of said methylparaben.

4. The solution as recited in claim 1, wherein said solution includes approximately 13 oz of said isopropyl alcohol.

5. The solution as recited in claim 1, wherein said solution includes approximately 0.9 oz of said methyl salicylate.

6. The solution as recited in claim 1, wherein said solution includes approximately 0.9 oz of said malic acid.

7. A method for treating the skin of human feet, consisting of:
    providing a treatment solution, wherein said treatment solution consists of:
    an amount of water;
    between approximately 40 oz and approximately 45 oz of magnesium sulfate per gallon of said water;
    between approximately 0.01 oz and approximately 1.0 oz of methylparaben per gallon of said water;
    between approximately 10 oz and approximately 15 oz of isopropyl alcohol per gallon of said water;
    between approximately 0.05 oz and approximately 1.5 oz of methyl salicylate per gallon of said water; and
    between approximately 0.05 oz and approximately 1.5 oz of malic acid per gallon of said water;
    applying said treatment solution to human feet.

8. The method as recited in claim 7, wherein said applying step is done through the use of a footbath.

9. The solution as recited in claim 7, wherein said magnesium sulfate is magnesium sulfate hepta-hydrate, $MgSO_4.7H_2O$.

* * * * *